(12) United States Patent
Zang et al.

(10) Patent No.: US 8,058,075 B2
(45) Date of Patent: Nov. 15, 2011

(54) MOLECULAR FLUORESCENCE SENSOR FOR HIGHLY SENSITIVE AND SELECTIVE DETECTION OF MERCURY

(75) Inventors: Ling Zang, Salt Lake City, UT (US); Yanke Che, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 76 days.

(21) Appl. No.: 12/634,037

(22) Filed: Dec. 9, 2009

(65) Prior Publication Data

US 2010/0144043 A1 Jun. 10, 2010

Related U.S. Application Data

(60) Provisional application No. 61/121,462, filed on Dec. 10, 2008.

(51) Int. Cl.
G01N 33/20 (2006.01)
C07D 471/04 (2006.01)
(52) U.S. Cl. ............. 436/81; 436/164; 544/296; 546/37
(58) Field of Classification Search ............... 436/81, 436/164; 544/296; 37/543
See application file for complete search history.

(56) References Cited

U.S. PATENT DOCUMENTS

| 7,138,121 B2 | 11/2006 | Spangler et al. |
| 7,332,283 B2 | 2/2008 | Lu et al. |
| 2005/0112769 A1 | 5/2005 | Lippard et al. |

OTHER PUBLICATIONS

Yanke Che et al., "Ultraselective fluorescent sensing of Hg2+ through metal coordination-induced molecular aggregation". Chem. Commun., 2008, 1413-1415. www.rsc.org/chemcomm.

Yanke Che et al., "Ultraselective Fluorescent Sensing of Hg2+ through Metal Coordination-Induced Molecular Aggregation". Royal Society of Chemistry 2008. S1-S3.

Jiaobing Wang and Xuhong Qian. "Two regioisomeric and exclusively selective Hg(II) sensor molecules composed of a naphthalimide fluorophore and an o-phenylenediamine derived triamide receptor". Chem Commun., 2006, 109-111. www.rsc.org/chemcomm.

(Continued)

*Primary Examiner* — Robert J Hill, Jr.
*Assistant Examiner* — Dwan A Gerido
(74) *Attorney, Agent, or Firm* — Gardner, Groff, Greenwald & Villanueva, PC.

(57) ABSTRACT

A fluorescent sensor compound based on a perylene core is described and disclosed. The fluorescent sensor compound for detecting mercury can have a structure I:

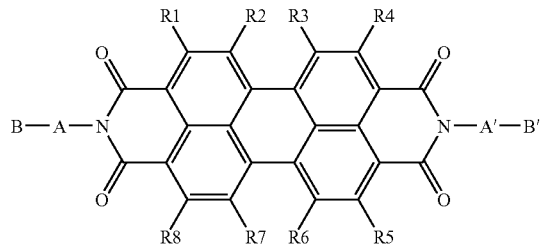

where A and A' are linking groups, B and B' are binding ligands which are selective for binding with $Hg^{2+}$, and R1 through R8 are side groups. These fluorescence sensor materials are robust against photobleaching, while still providing exceptional detection sensitivity and selectivity.

20 Claims, 5 Drawing Sheets

OTHER PUBLICATIONS

Chuihong Li et al., "Synthesis of a Novel Poly(para-phenylene ethynylene) for Highly Selective and Sensitive Sensing Mercury (II) Ions". Journal of Polymer Science: Part A: Polymer Chemistry, vol. 26, 1998-2007 (2008).

Song Young, "Selective fluorescent Hg (II) detection in aqueous solutions with a dye intermediate" Spectrochimica Acta Part A 68 (2007) 705-709.

Feng, KE et al., "A potential Fluorescent Hg(II) chemosensor", Microchemical Journal 81 (2005) 23-27.

MOLECULAR FLUORESCENCE SENSOR FOR HIGHLY SENSITIVE AND SELECTIVE DETECTION OF MERCURY

RELATED APPLICATIONS

This application claims benefit of U.S. Provisional Application No. 61/121,462, filed Dec. 10, 2008 which is incorporated herein by reference.

GOVERNMENT INTEREST

This invention was made with government support under Grants CHE0641353 and CBET730667 awarded by the National Science Foundation. The Government has certain rights to this invention.

FIELD OF THE INVENTION

This invention relates generally to fluorescent materials and the use of such materials for detection of mercury. Therefore, the present invention relates generally to the fields of fluorescence chemistry and materials science.

BACKGROUND OF THE INVENTION

As a highly toxic metal ion, $Hg^{2+}$ causes serious health and environmental problems. Many kinds of chemical and physical sensors have been developed for the detection of $Hg^{2+}$, among which fluorescence based sensing represents a simple, but sensitive technique providing detection limits of as low as ppb. However, improvement of the detection selectivity in the context of interference from coexisting metal ions remains challenging. Indeed, the concentrations of the common coexisting metal ions are usually much higher than the concentration of $Hg^{2+}$, for which the safety level set for drinking water by the EPA is only 2 ppb (or 10 nM). To detect such trace amounts of $Hg^{2+}$ with minimal false positives, a sensor technique with extremely high selectivity can be useful.

Recently, the selective complexation between thymine and $Hg^{2+}$ has been employed successfully to develop selective sensors for the detection of $Hg^{2+}$ ions based on fluorescence resonance energy transfer and a colorimetric method. However, both of these sensing systems involve the tedious synthesis of the DNA oligomers and chemical functionalization with different fluorophores (energy donor and acceptor) and nanoparticles. Such processes present a technical hurdle to expedient, cost-effective applications. Moreover, the multiple binding sites within the DNA strands may complicate the chemical process and cause a mismatch in complexation with $Hg^{2+}$. A DNA strand containing more than four thymine moieties may function as a multidentate ligand that enables effective binding with transition metal ions, such as $Zn^{2+}$, $Cu^{2+}$, $Ni^{2+}$, etc. When these metal ions exist in large excess (as they usually do) compared to the concentration of $Hg^{2+}$, the binding with $Hg^{2+}$ will become less competitive, leading to a decreased selectivity for the sensing.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention and they are, therefore, not to be considered limiting of its scope. It will be readily appreciated that the components of the present invention, as generally described and illustrated in the figures herein, could be arranged, sized, and designed in a wide variety of different configurations. Nonetheless, the invention will be described and explained with additional specificity and detail through the use of the accompanying drawings in which:

DETAILED DESCRIPTION

Figure 1:
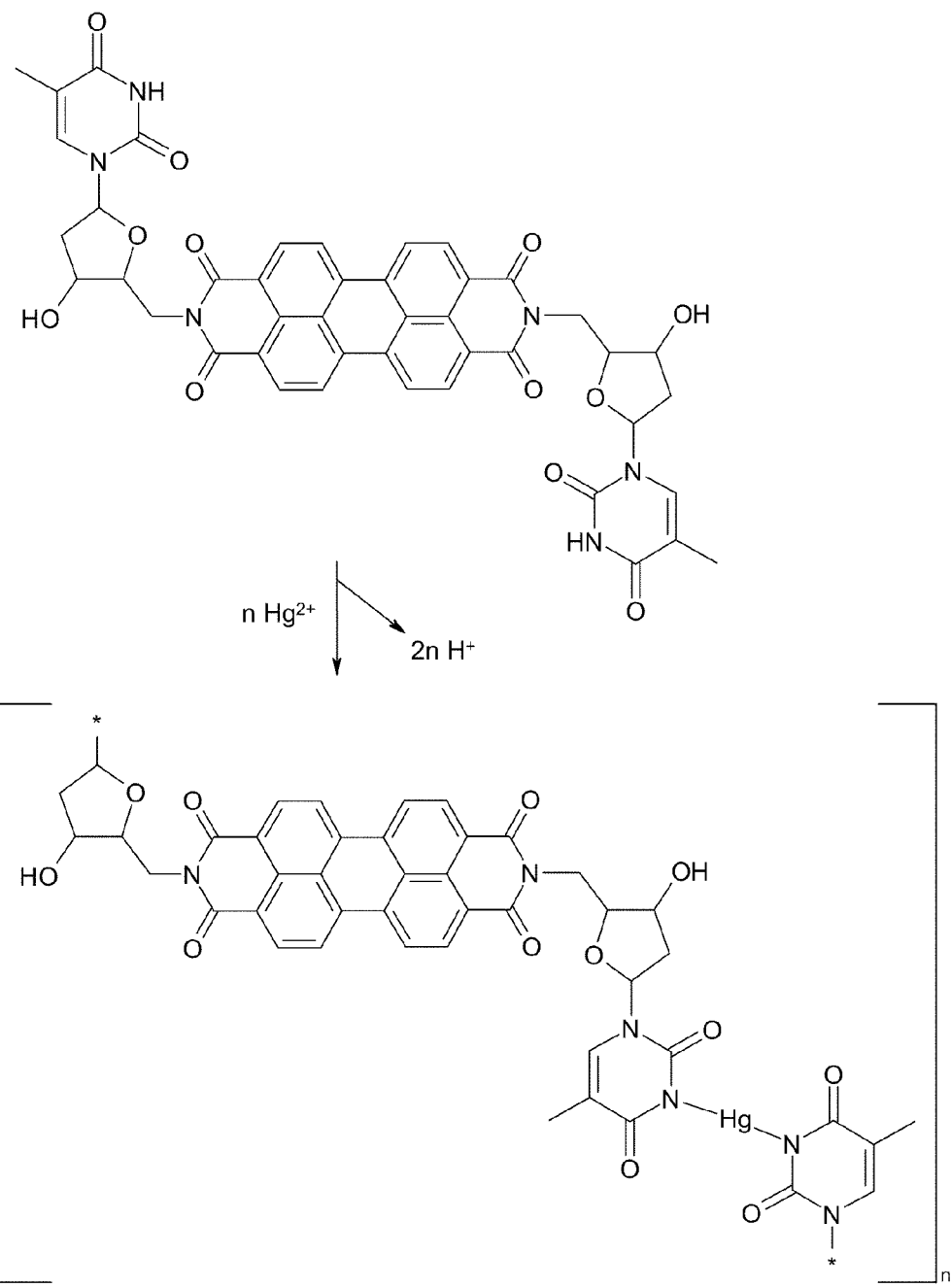
FIG. 1 is the molecular structure of the sensor molecule, TT-PTCDI and coordination with $Hg^{2+}$. The linear coordination of T-Hg-T leads to polymerization (in a 'z' or zig-zag pattern) and eventually aggregation of the PTCDI molecules. Energy minimization was achieved by DFT calculation (B3LYP/6-31 g*) using Gaussian 03.

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

DEFINITIONS

In describing and claiming the present invention, the following terminology will be used.

The singular forms "a," "an," and "the" include plural referents unless the context clearly dictates otherwise. Thus, for example, reference to "a binding ligand" includes reference to one or more of such groups and reference to "exposing" refers to one or more such steps.

As used herein, "alkylene" refers to a saturated hydrocarbon having two valencies, i.e. for bonding with adjacent groups. Non-limiting examples of alkylenes include —CH—, —CH$_2$—, —C$_2$H$_4$—, —C$_3$H$_6$—, etc.

As used herein, when referring to a component of a composition, "primarily" indicates that that component is present in a greater amount than any other component of the relevant composition.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims unless clearly indicated otherwise. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Perylene Based Fluorescent Sensors

In light of the problems and deficiencies noted above, fluorescence sensor materials which are robust against photobleaching can be provided, while still providing exceptional detection sensitivity and selectivity. Such a sensing mechanism can be based on modulation of the fluorescence emission of the sensory materials upon binding with mercury ions. A suitable fluorescent sensor compound for detecting mercury can have structure I:

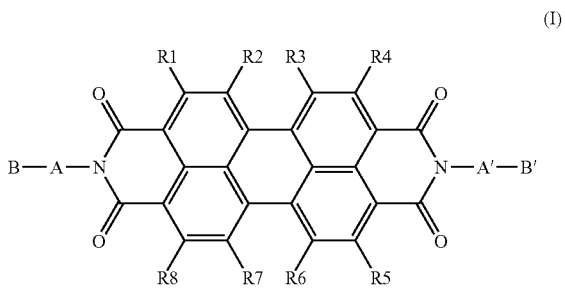

where A and A' are linking groups, B and B' are binding ligands which are selective for binding with Hg$^{2+}$, and R1 through R8 are side groups.

The above perylene tetracarboxylic diimide (PTCDI) core functions as the central part for signal transaction, e.g. as the fluorophore. Typically, the PTCDI core can have hydrogen as each of the side groups R1-R8. However, one or more side groups can be substituted for these hydrogens, as long as such side groups do not destroy the selective binding and fluorescence properties of the compound. Non-limiting examples of such side groups can include C1-C8 alkyl groups (e.g. butyl group, including branched alkyls), carboxylate groups (for improved water solubility), or any other groups that do not damage the binding (to Hg$^{2+}$) and sensing functionality, but afford sufficient or better water solubility of the whole molecule. Good water solubility is conducive to detection kits or assays that are suited for application in aqueous samples.

The linking group and binding ligand can generally meet some basic requirements to afford the desired sensing performance. The linking groups can generally contribute to increasing the water solubility of the whole molecule, especially for most applications where sensing is under aqueous environments. Furthermore, desirable linking groups can enable easy synthesis of the molecule and maintain flexibility between the binding moiety and the PTCDI core which facilitates binding with mercury ions. Generally, linking groups can be hydrophilic and have at least one single bond about which the linking group can allow the sensor compound to rotate. In one aspect, the linking groups A and A' can be independently selected from the group consisting of:

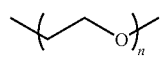

wherein n is 1 to 3,

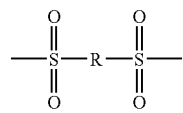

where R is a C1 to C8 alkylene,

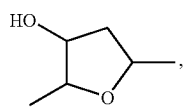

and
combinations of these groups.

Other linking groups can also be suitable such as, but not limited to, sugars having less than 10 carbons (e.g. glucose, fructose, galactose, mannose, and the like), and H or C1-C4 alkyl substituted groups of the linking groups listed above. In one specific aspect, the linking group can have the formula

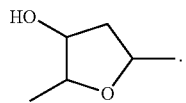

Generally, the linking groups A and A' can be the same, although this is not always required.

A variety of ligands can be suitable for the binding ligands. Some considerations for a suitable binding ligand include formation of a 2:1 (2 ligands+1 mercury) complex. This 2:1 ratio can contribute to a linear polymerization of the fluorescent sensor compound molecules upon binding to mercury ions. In addition, strong binding to the mercury ions facilitates a low detection limit. Furthermore, a high selectivity of binding to mercury ions against interference of co-existing metal ions can minimize false positives. A particularly effective binding ligand is thymine and its derivatives having structure (II),

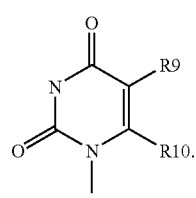

where R9 and R10 can be appropriate substituents that don't damage the selective and strong binding with $Hg^{2+}$, but afford sufficient or better water solubility of the whole molecule. Substituents R9 and R10 can be independently selected from groups such as, but not limited to, H, $CH_3$, C2-C4 alkyls, alkyl alcohols, that do not possess amine, carboxylate or groups that bind to $Hg^{2+}$ and other metal ions with no selectivity, and thus interfere with the intrinsic binding of the thymine that provides selective recognition of $Hg^{2+}$. As with the linking group, each of B and B' can be the same, although different groups could be used. Each of the binding ligands can have a 2:1 binding ratio with $Hg^{2+}$. In one aspect, the binding ligand is thymine (e.g. where R9 is $CH_3$ and R10 is H).

The fluorescent sensor compounds can be formed using any suitable synthesis technique. Although other approaches can be suitable, one approach involves obtaining the PTCDI core material from a commercial source such as Sigma Aldrich or others. This PTCDI core can then be reacted with suitable reagents to obtain the sensor compound. The reagents can include the linking and binding ligand groups combined. Alternatively, the linking group can be first attached to the imide sites, followed by attachment of the binding ligands to the linking groups. The reagents can include, but are not limited to, a flexible linkage covalently connected to the thymine based binding ligand (II), wherein the flexible linkage can be a molecular structure that does not damage the binding (to $Hg^2$) and sensing functionality, but afford sufficient or better water solubility of the whole molecule. For example, the flexible linkage can be independently selected from the group consisting of:

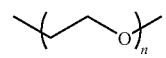

wherein n is 1 to 3,

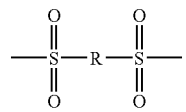

where R is a C1 to C8 alkylene,

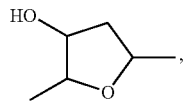

and
combinations of these groups.

Non-limiting examples of reactions can include condensation reactions and any other organic chemical reaction protocols that are suited for making the flexible linkage and the thymine binding ligands, and coupling them together to form the reagent suited to react to the PTCDI core to produce the final sensor molecule. The resulting products can optionally be filtered and/or washed, followed by running silica gel and aluminum oxide column chromatography to increase purity before use.

In practice, the fluorescent sensor compound is most often a solid in its pure form. For use as a sensor, the fluorescent sensor compound can be dissolved in a suitable aqueous solution. At least some sensor compounds fitting Structure I are only partially or poorly soluble in water. In order to improve solubility, the aqueous solution can further include an organic solvent. For example, the fluorescent sensor compound can be initially mixed with and dissolved in the organic solvent and then the water added. Non-limiting examples of suitable organic solvents can include dimethyl formamide, tetrahydrofuran, dimethyl sulfoxide, dioxane, and combinations thereof. In one aspect, the organic solvent can be dimethyl formamide. Although the specific amount of organic solvent can vary depending on the specific materials, generally the organic solvent can be present from about 40 vol % to about 90 vol % of the solution, and typically about 70 vol %. However, some fluorescent sensor compounds can allow for higher water content.

A method of detecting mercury ion ($Hg^{2+}$) in a fluid can include exposing the fluorescent sensor compound to a fluid sample. The fluid sample can be any fluid for which mercury content needs to be assessed. This could be a wastewater effluent, river, pond, groundwater, lab samples, and the like. The presence of mercury can be assessed by displaying a fluorescence change upon exposure of the sensor compound to the fluid sample. This can be a visible change in fluorescence, an indicator change, and/or a numerical output. For numerical quantitative measure of mercury content, a fluorometer can be used to measure changes in fluorescence before and after exposure to the fluid. Alternatively, the displaying can be qualitative. In one example, the presence of mercury can be visually assessed based on a visible decrease in fluorescence of the fluorescent sensor compound. In other embodiments, as the fluorescent sensor compound binds with mercury, the complexed molecules tend to aggregate and polymerize to form visible particles. Generally, a solution of the sensor compound can be mixed with the fluid sample. An alternative approach is to disperse the sensor compound in a support matrix, e.g., agarose gel (commercially available) or other porous hydrophilic materials that possess strong accessibility to water and large enough pore size to host the sensor molecules and allow for polymerization upon binding to mercury ion ($Hg^{2+}$). The whole composite can be made in a format of testing kit. In this case, the mercury test can be performed by dipping such a kit into the water sample that contains mercury ion ($Hg^{2+}$) or alternatively dropping a small amount of the water sample onto the kit.

One aspect of the sensor compounds is an ability to be easily regenerated and reused. The fluorescent sensor compound can be regenerated by flushing with an acid sufficient to remove bound $Hg^{2+}$. The result is an unbound fluorescent sensor compound which can be reused. Although almost any acid can be used, hydrochloric acid is effective and inexpensive. Most often the regenerating can be substantially completely reversible, although some material loss may be expected depending on the process and care taken during regeneration and use.

EXAMPLE

Dideoxythymidine-perylene-3,4,9,10-tetracarboxylic diimide (TT-PTCDI) was synthesized via the condensation method. Briefly, 3.6 mg (9.2 µmol) 3,4,9,10-perylene-tetracarboxylic dianhydride (Aldrich), 5 mg (21 µmol) 5'-amino-5'-deoxythymidine (Sigma), and 0.6 g imidazole (Fisher) were heated under argon at 120° C. for 3 hours to form a precursor sensor compound. The reaction mixture was cooled to room temperature and dispersed in 10 mL ethanol, followed by addition of 20 mL 2 M HCl in order to close the side ring structure to form the imide compound. The mixture was stirred overnight. The resulting red solid was collected by vacuum filtration through a 0.45 µm membrane filter (Osmonics). The solid was then washed thoroughly with distilled water until the pH of washings turned to neutral. The collected fluorescent compound solid was dried in vacuum at 60° C. TLC: Rf (silica gel/dioxane:$CHCl_3$=75:25)=0.83. All other chemicals were used as received.

Due to the limited solubility of TT-PTCDI in common NMR solvents, it was challenging to run NMR measurements on this compound. Mass spectra were run on a MALDI instrument using angiotensin as an external standard. MS ($M+2H^+$), m/z: 840.29 (calc. 840.22). UV-visible absorption spectra were recorded on a Perkin Elmer Lambda 25 spectrophotometer. Fluorescence spectra were measured using a Perkin Elmer LS55 fluorometer.

The sensor molecule, N,N'-dideoxythymidine-3,4,9,10-perylene-tetracarboxylic diimide (TT-PTCDI), represents a robust class of fluorophore with extremely high fluorescence yield (close to 100% in organic solvents). The high photostability of PTCDI molecules provides the sensor with additional credits in terms of sustainability and reproducibility in real applications, where repeated measurements are usually required to avoid false positives. One unique property of PTCDI molecules is that the fluorescence of the individual molecules diminishes dramatically when the molecules are associated into an aggregate state. Without being bound to any one particular theory, the cause of such efficient fluorescence quenching appears to be the strong intermolecular pi-pi interaction between the PTCDI backbones. Particularly, TT-PTCDI possesses a 'Z' structure that favors linear intermolecular coordination with $Hg^{2+}$, which enables chain polymerization of the molecules, eventually leading to aggregation of the whole molecular system.

The molecular aggregation induced fluorescence quenching found in this example is in sharp contrast to the more common fluorescent sensing systems, for which the photoinduced electron transfer (between the fluorophore and the targeted species) usually dominates the quenching mechanism. Indeed, for the sensor molecule shown in FIG. 1 it is unlikely that such an electron transfer will occur, mainly because of the large spatial distance between the bound mercury and the PTCDI backbone, where the linker is primarily composed of s-bonds.

Figure 2:
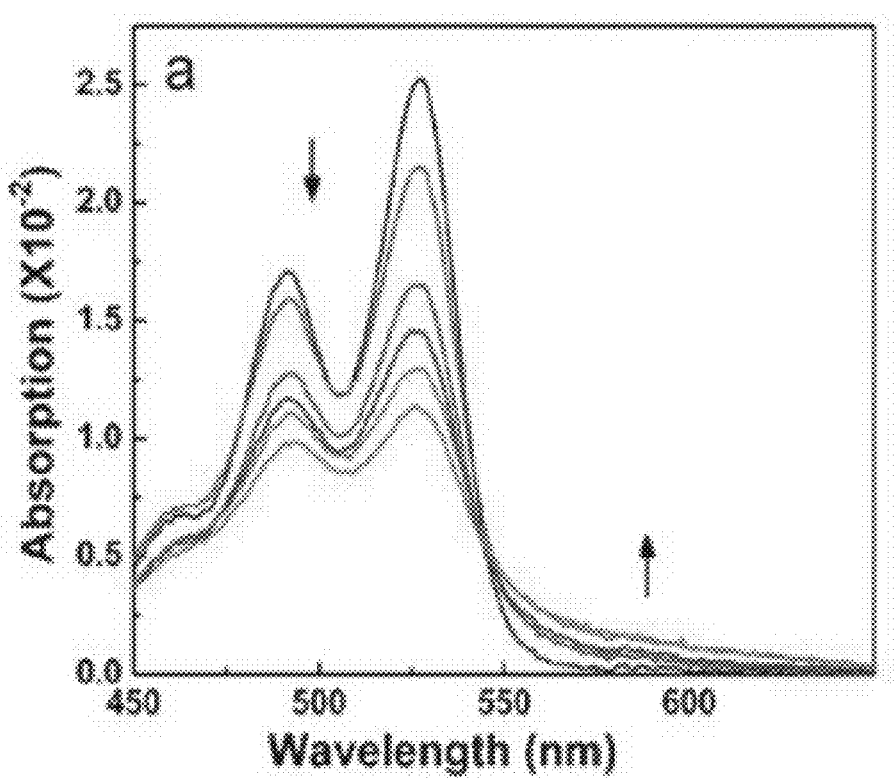
FIG. 2 shows absorption spectra of 1.0 µM TT-PTCDI solution in DMF-$H_2O$ (70:30, vol.) in the presence of various concentrations of $Hg^{2+}$ (0, 0.38, 0.63, 0.83, 1.23 and 1.73 µM).

FIG. 2 shows the absorption spectral change of a 1.0 µM solution of TT-PTCDI dissolved in 70:30 (vol.) DMF-$H_2O$ upon addition of $Hg^{2+}$ ions. With an increase in the concentration of $Hg^{2+}$ the absorption bands due to the individual molecules decrease, while a new band emerges and increases at the longer wavelength, which is characteristic of the aggregation state of PTCDI molecules. An isosbestic point was clearly observed around 545 nm, indicating the stoichiometric conversion of the free molecules into the aggregation state. Indeed, with addition of about two-fold excess of $Hg^{2+}$ ions all the TT-PTCDI molecules were eventually precipitated out and turned out to be visible dark red flocs, leaving the rest of the solution totally colorless. Moreover, these flocs can be redissolved back to the solution simply by addition of acid, which breaks up the T-Hg-T coordination by reprotonation of the thymine moiety, i.e., shifting the reaction equilibrium shown in FIG. 1 to the left.

Figure 3:
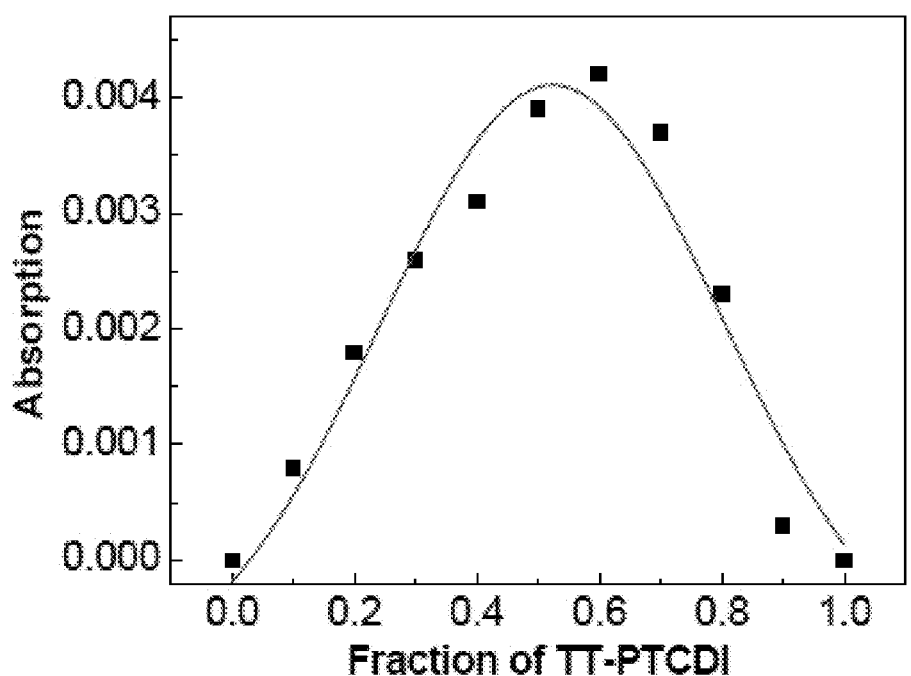
FIG. 3 is a Job's plot of the complexation between TT-PTCDI and $Hg^{2+}$. Total concentration of TT-PTCDI and $Hg^{2+}$ was kept constant at 1 µM in DMF/$H_2O$ (70/30, vol) solution.

The 1:1 complexation between $Hg^{2+}$ and TT-PTCDI was confirmed by a Job's plot (FIG. 3), which was obtained by measuring the difference in absorption at 527 nm with the change in molar fraction of TT-PTCDI. The effective molecular aggregation resulted in a dramatic decrease in fluorescence intensity as depicted in FIG. 4, mainly owing to the strong p-p interaction between the tightly packed PTCDI molecules within the aggregate.

Figure 4:
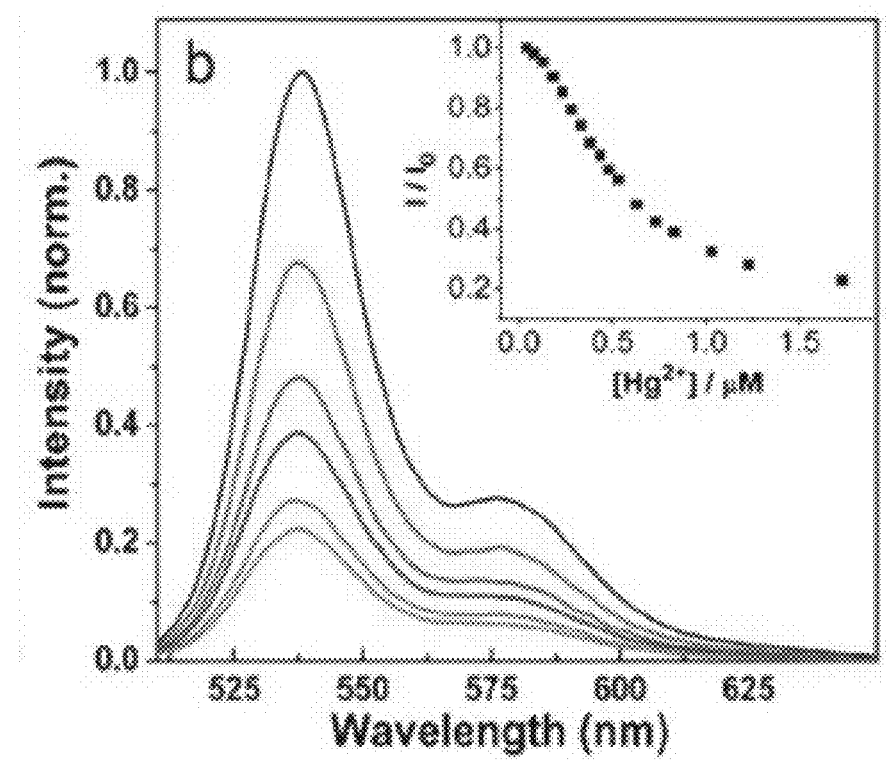
FIG. 4 shows fluorescence spectra of 1.0 µM TT-PTCDI solution in DMF-$H_2O$ (70:30, vol.) in the presence of various concentrations of $Hg^{2+}$ (0, 0.38, 0.63, 0.83, 1.23 and 1.73 µM). Inset shows relative intensity ($1_{max}$ 538 nm) vs. the concentration of $Hg^{2+}$.

The fluorescence titration shown in FIG. 4 was also conducted in DMF solutions with varying volume fractions of water to investigate the effect of solvent property on the fluorescence quenching efficiency. Since the binding affinity between $Hg^{2+}$ and TT-PTCDI is determined by the solubility of both species ($Hg^{2+}$ is more soluble in water, whereas TT-PTCDI is predominantly soluble in DMF), there is an optimal volume fraction of water in DMF that provides the maximum fluorescence quenching. Indeed, upon examination for various volume fractions ranging from 0% to 50% the optimal fluorescence quenching was observed for the solvent containing 30% water, the binary solvent used in FIGS. 2 and 4. Such a water-containing sensor system can be highly desirable for applications of the sensor in aqueous environments, where $Hg^{2+}$ ions usually exist.

Figure 5:
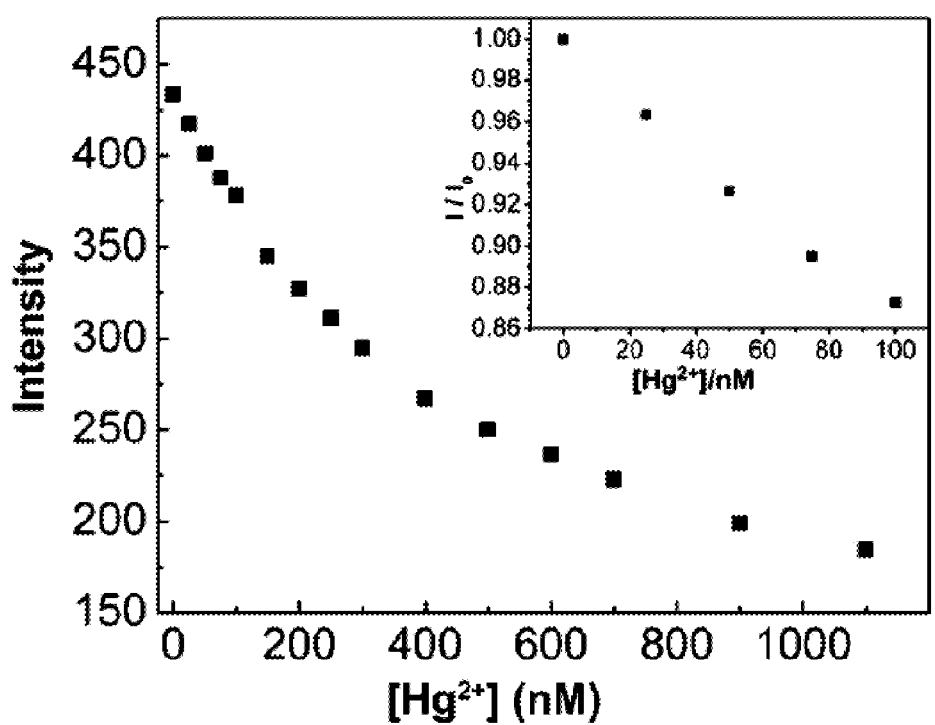
FIG. 5 shows fluorescence quenching of a 0.1 µM solution of TT-PTCDI in DMF-$H_2O$ (70:30, vol.) by various concentrations of $Hg^{2+}$: fluorescence intensity (at $1_{max}$=538 nm) as a function of the concentration of $Hg^{2+}$. Inset: relative intensity ($I/I_0$) vs. the concentration of $Hg^{2+}$ in the low concentration region up to 100 nM, showing the detection limit of $Hg^{2+}$ around 5 nM, corresponding to a 1% decrease in the fluorescence intensity.

With the 70:30 (vol.) DMF-$H_2O$ solvent the detection limit can be determined by decreasing the concentration of TT-PTCDI. Within a certain concentration range (where effective binding between $Hg^{2+}$ and the thymine ligand still exists as determined by the binding affinity), it is generally true that the lower the concentration of the fluorophore, the less quencher is required for the same percentage of fluorescence quenching. For a 0.1 µM solution of TT-PTCDI as low as 5 nM (or below) of $Hg^{2+}$ can be feasibly detected considering the fact that a well-calibrated photodetector can reliably measure an intensity change down to 1% or lower (FIG. 5).

The high sensitivity thus obtained is consistent with the strong complexation of T-Hg-T, for which $Hg^{2+}$ binds to the thymine by replacing the proton at the secondary amine (FIG. 1), in a manner similar to metallic coordination within a porphyrin.

Figure 6:
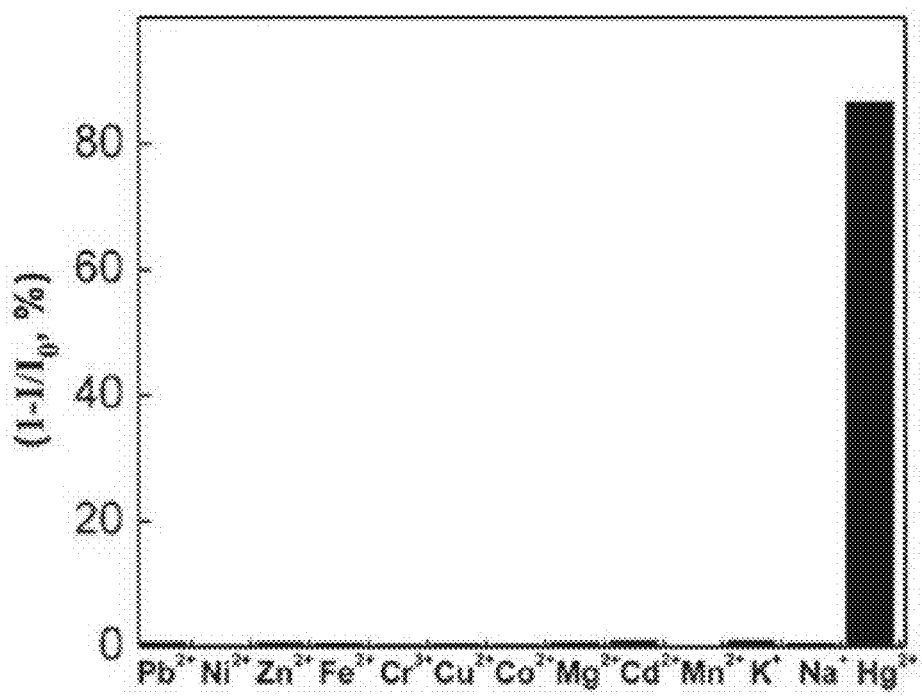
FIG. 6 shows fluorescence response of TT-PTCDI (1.0 µM) to $Hg^{2+}$ (3.5 µM) and various other metal ions (12.5 µM) in DMF-$H_2O$ (70:30, vol.) solutions. The bars represent the percentage of fluorescence quenched ($1-I/I_0$).
Figure 7:
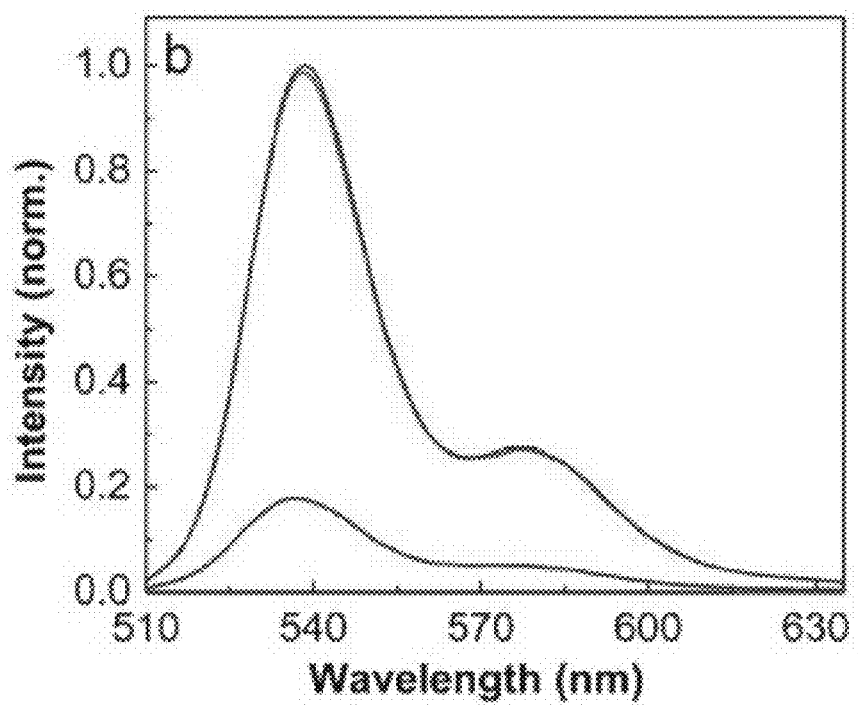
FIG. 7 shows fluorescence spectra of a 1.0 µM TT-PTCDI solution in the absence (black) and presence (red) of a mixture of all 12 metal ions (each 12.5 µM). Addition of 3.5 µM $Hg^{2+}$ to the mixed solution resulted in a dramatic fluorescence quenching (blue).

Since the linear coordination of T-Hg-T is extremely selective for $Hg^{2+}$, the presence of other metal ions should not produce fluorescence quenching similar to that observed for $Hg^{2+}$. Indeed, as tested for the environmentally relevant metal ions including $Cu^{2+}$, $Ni^{2+}$, $Fe^{2+}$, $Co^{2+}$, $Pb^{2+}$, $Cd^{2+}$, $Zn^{2+}$, $Mn^{2+}$, $Cr^{3+}$, $Mg^{2+}$, $Ca^{2+}$, $K^+$ and $Na^+$, none of these ions demonstrated a positive response to the same sensing system depicted in FIG. 2. As shown in FIG. 6, even at relatively higher concentration (e.g., 12.5 µM) the fluorescence decrease observed for all these background ions was around only 1% or below, whereas ca. 87% fluorescence quenching was observed in the presence of only 3.5 µM $Hg^{2+}$. Such a high selectivity was further tested in an extreme case as presented in FIG. 7, where a mixture of all the metal ions mentioned above (each at 12.5 µM) was added to the sensing system, and resulted in almost no change in the fluorescence intensity. However, addition of 3.5 mM $Hg^{2+}$ to the mixed solution led to ca. 83% quenching of the fluorescence.

Figure 8:
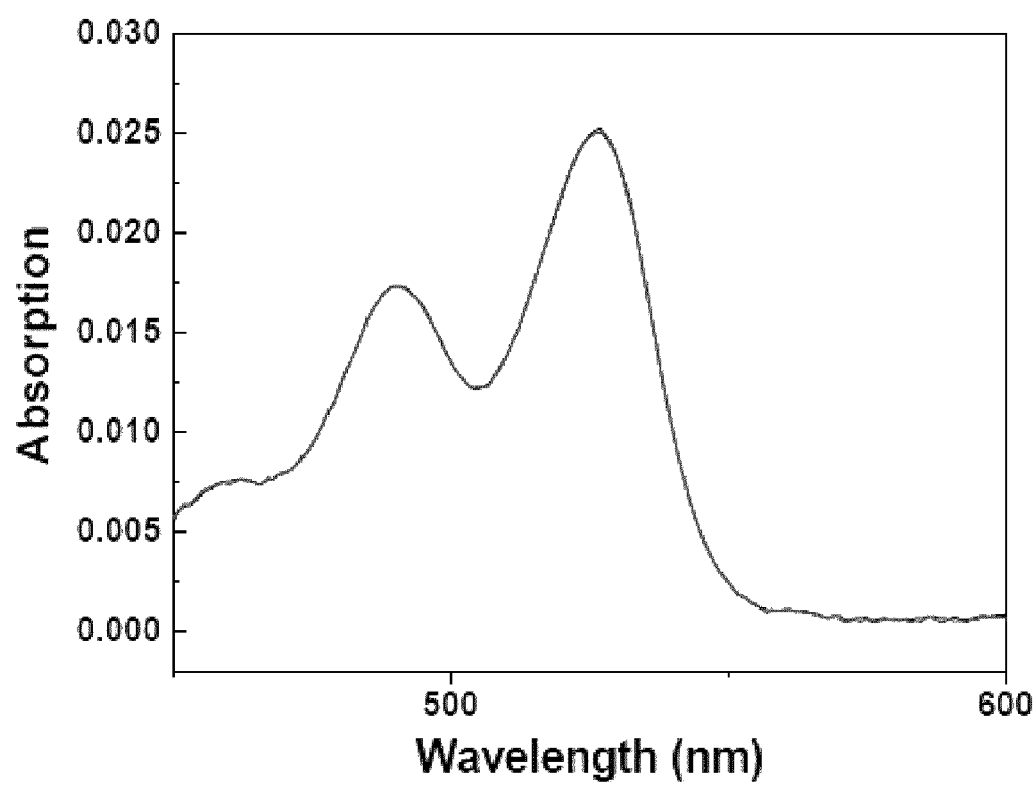
FIG. 8 is an absorption spectra of a 1 µM solution of TT-PTCDI in DMF/$H_2O$ (70:30, vol.) in the absence (black) and presence of 12.5 µM $Cu^{2+}$ (red), showing no significant change in absorption. Similar results were obtained for all the other environmentally relevant metal ions including $Ni^{2+}$, $Fe^{2+}$, $Co^{2+}$, $Pb^{2+}$, $Cd^{2+}$, $Zn^{2+}$, $Mn^{2+}$, $Cr^{3+}$, $Mg^{2+}$, $Ca^{2+}$, $K^+$ and $Na^+$.

Consistent with these fluorescence observations, no significant change was observed for the absorption spectra of the TT-PTCDI solution upon addition of the background ions (FIG. 8). Indeed, no precipitation was observed for the TT-PTCDI solution in the presence of any of the interfering ions. The ultrahigh selectivity thus obtained for the sensor can help avoid the false positives in dynamic field use conditions, where detection of $Hg^{2+}$ is often interfered with by other transition metal ions (particularly when they are present in much higher concentrations).

This ultrahigh selectivity and sensitivity thus obtained can also be used in a sensor assay, which can find broad application in both environmental monitoring and clinical diagnostics. For example, fluorescent sensor compounds can be used in applications of EPA authorities and other water/air QC labs where frequent monitoring of water/air quality (against mercury) with high accuracy is needed. One application of this sensor system is to help solve the emerging problem of mercury pollution in the Great Salt Lake area. Monitoring the mercury pollution and examining the pollution sources require huge amount of work of sampling and analysis. The sensor system can also be applied to clinical labs, where toxicity test of $Hg^{2+}$ are needed.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A fluorescent sensor compound for detecting mercury having a structure I:

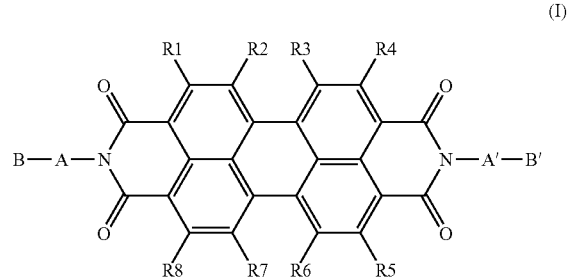

where A and A' are linking groups, B and B' are binding ligands which are selective for binding with $Hg^{2+}$, and R1 through R8 are side groups.

2. The fluorescent sensor compound of claim 1, wherein A and A' are the same.

3. The fluorescent sensor compound of claim 1, wherein B and B' are thymine having a structure (II)

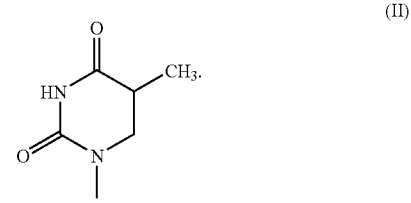

4. The fluorescent sensor compound of claim 1, wherein B and B' are the same.

5. The fluorescent sensor compound of claim 1, wherein the binding ligands each have a 2:1 binding ratio with $Hg^{2+}$.

6. The fluorescent sensor compound of claim 1, wherein the R1 through R8 are each hydrogen.

7. The fluorescent sensor compound of claim 1, wherein the R1 to R8 are, independently, hydrogen or C1-C8 alkyl.

8. The fluorescent sensor compound of claim 1, wherein R1 to R8 are each hydrogen, wherein A and A' have the formula

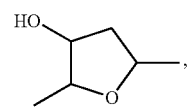

and B and B' are thymine having a structure (II)

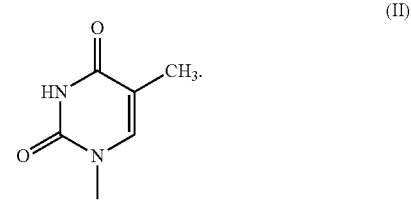

9. The fluorescent sensor compound of claim 1, wherein A and A' are independently selected from the group consisting of

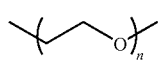

wherein n is 1 to 3,

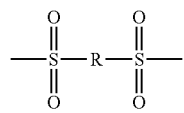

where R is a C1 to C8 alkylene,

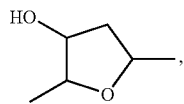

C1-C4 alkyl derivatives thereof, and combinations thereof.

10. The fluorescent sensor compound of claim 9, wherein A and A' have the formula

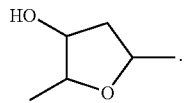

11. A fluorescent sensor solution including an aqueous solution of the fluorescent compound of claim 1.

12. The solution of claim 11, further comprising an organic solvent.

13. The solution of claim 12, wherein the organic solvent is selected from the group consisting of dimethyl formamide, tetrahydrofuran, dimethyl sulfoxide, dioxane, and combinations thereof.

14. The solution of claim 12, wherein the organic solvent is present from about 40 vol % to about 90 vol % of the solution.

15. A method of detecting mercury ion ($Hg^{2+}$) in a fluid, comprising:
a) exposing the fluorescent sensor compound of claim 1 to a fluid sample; and
b) displaying a fluorescence change upon exposure of the sensor compound to the fluid sample.

16. The method of claim 15, wherein the fluorescence change is further measured by a fluorimeter.

17. The method of claim 15, wherein the displaying step (b) is a quantitative measure of fluorescence response.

18. The method of claim 15, wherein the displaying step (b) is qualitative.

19. The method of claim 15, further comprising regenerating the fluorescent sensor compound by flushing with an acid sufficient to remove bound $Hg^{2+}$.

20. The method of claim 19, wherein the acid is hydrochloric acid.

* * * * *